United States Patent  
McCusker et al.

(10) Patent No.: US 9,637,133 B1
(45) Date of Patent: May 2, 2017

(54) OPERATOR CAPACITY MONITOR AND ENGAGEMENT OF EMERGENCY ACTION SYSTEM AND METHOD

(71) Applicant: Rockwell Collins, Inc., Cedar Rapids, IA (US)

(72) Inventors: Patrick D. McCusker, Walker, IA (US); Talha S. Ansari, Marion, IA (US); John M. Connelly, Cedar Rapids, IA (US)

(73) Assignee: Rockwell Collins, Inc., Cedar Rapids, IA (US)

( * ) Notice: Subject to any disclaimer, the term of this patent is extended or adjusted under 35 U.S.C. 154(b) by 85 days.

(21) Appl. No.: 14/822,565

(22) Filed: Aug. 10, 2015

(51) Int. Cl.
   *G08B 23/00* (2006.01)
   *B60W 40/08* (2012.01)

(52) U.S. Cl.
   CPC ..... *B60W 40/08* (2013.01); *B60W 2040/0818* (2013.01)

(58) Field of Classification Search
   CPC ............... B60W 40/08; B60W 2040/0818

USPC ......................................................... 340/576
See application file for complete search history.

(56) References Cited

U.S. PATENT DOCUMENTS

2016/0082838 A1* 3/2016 Melas ................ G06K 9/00845
                                                    340/575

* cited by examiner

*Primary Examiner* — Tanmay Shah
(74) *Attorney, Agent, or Firm* — Angel N. Gerdzhikov; Donna P. Suchy; Daniel M. Barbieri

(57) ABSTRACT

A system and method may monitor an operator of a vehicle for signs of incapacity. Low cost electronic devices may monitor operator vital signs allowing the system to determine when the operator is active and normally operating the vehicle, operating the vehicle under a high workload, and/or has become inactive (potentially incapacitated). Industrial electronics may enable to system to monitor ambient workspace temperature, pressure, and oxygen levels and may offer the system an additional second source of information to detect ambient factors affecting the capacity of the operator. Should operator capacity be in question, the system may warn the operator and take an appropriate safety based action including application of a control and eventually assuming control of the vehicle.

19 Claims, 4 Drawing Sheets

OPERATOR CAPACITY MONITOR AND ENGAGEMENT OF EMERGENCY ACTION SYSTEM AND METHOD

FIELD OF THE INVENTIVE CONCEPTS

Embodiments of the inventive concepts disclosed herein relate generally to monitoring a capacity of an operator of a vehicle. More particularly, embodiments of the inventive concepts disclosed herein relate to a system and related method for physical monitoring of an operator as well as monitoring of an environment in which the operator is physically located and execution of an emergency action should the monitoring reveal an abnormality.

BACKGROUND

In single operator vehicles, early detection of operator incapacitation may be one method to reduce accidents. Some examples of single operator vehicles may include a small business aircraft as well as a current military fighter aircraft and a commuter train. Incapacitation of the single operator may lead to dire consequences.

Traditional operator monitoring solutions may employ a pulse oximeter system physically temporarily attached to the finger of the single operator to measure blood oxygen saturation. During high workload where the operator may need the use of the finger, these devices are problematic as they interfere with the operator's ability to manipulate controls and/or change the position of a switch. These traditional devices may also be limited to measuring one parameter of interest (oxygen saturation) which can detect oxygen deprivation caused by, for example, a slow depressurization event in an aircraft. However, theses traditional devices are unable to detect additional sources of threats to the cognizance and consciousness of the single operator.

Therefore, a need remains for method and system capable of early recognition of a single operator physical incapacitation and follow on action to ensure the safety of the single operator as well as the vehicle, passengers and cargo therein.

SUMMARY

In one aspect, embodiments of the inventive concepts disclosed herein are directed to a method for monitoring a capacity of an operator. The method may comprise accessing an acceptable range for an operator physical parameter. The method may also establish a data connection with an operator physical monitor configured for measuring a physical parameter of an operator of a vehicle. The method may periodically receive an operator physical parameter via the data connection with the operator physical monitor, comparing the received operator physical parameter with the acceptable range.

The method may send a first warning to the operator via a warning device if a result of the comparing includes an operator physical parameter outside of the acceptable range. Should the first warning fail to rectify the situation, the method may execute an emergency action if a result of the comparing continues to include an operator physical parameter outside of the acceptable range. Here, the execution of the emergency action may be delayed by a variable delay to enable the operator to intervene. The emergency action may include 1) sending a second warning to the operator, 2) executing a vehicle maneuver to ensure a safety of the vehicle and a safety of the operator, and 3) sending a notification offboard the vehicle.

In a further aspect, embodiments of the inventive concepts disclosed herein are directed to a method further including acquiring an operator specific detail, acquiring an operational status of the vehicle, and adjusting the acceptable range based on the received operator specific detail and the operational status of the vehicle.

In a further aspect, embodiments of the inventive concepts disclosed herein are directed to a method wherein acquiring an operator specific detail further includes acquiring the operator specific detail from the data connection with an operator physical monitor, an input from the operator, and from a memory.

In a further aspect, embodiments of the inventive concepts disclosed herein are directed to a method further including accessing an acceptable range for an operator workspace ambient parameter, establishing a data connection with a workspace ambient monitor configured for measuring the operator workspace ambient parameter, periodically receiving an operator workspace ambient parameter from the workspace ambient monitor, comparing the operator workspace ambient parameter with the acceptable range, and executing the emergency action if a result of the comparing includes 1) an operator workspace ambient parameter outside of the acceptable range and 2) an operator physical parameter outside of the acceptable range, the execution of the emergency action after the variable delay.

In a further aspect, embodiments of the inventive concepts disclosed herein are directed to a method wherein the operator physical parameter further includes a pulse rate, a respiration rate, a skin temperature, an activity level, and a perspiration level, and the operator workspace ambient parameter further includes an air temperature, a motion level, an air pressure, a humidity level, and an oxygen level.

In a further aspect, embodiments of the inventive concepts disclosed herein are directed to a method further including establishing a data connection with an interactive workspace display onboard the vehicle, accessing an acceptable interactivity rate for the operator with the interactive workspace display, the acceptable interactivity rate including a phase of operations of the vehicle, receiving a current interactivity rate from the interactive workspace display, comparing the current interactivity rate with the acceptable interactivity rate, and sending the first warning to the operator via the warning device if a result of the comparing includes a current interactivity rate outside the acceptable interactivity rate for the phase of operations.

In a further aspect, embodiments of the inventive concepts disclosed herein are directed to a method further comprising receiving an acceptable range for an external ambient parameter, establishing a data connection with ambient monitor configured for measuring the external ambient parameter, receiving the external ambient parameter from the ambient monitor, and comparing the external ambient parameter to the acceptable range, and sending the first warning to the operator via the warning device if a result of the comparing includes an external ambient parameter outside the acceptable range.

In a further aspect, embodiments of the inventive concepts disclosed herein are directed to a method wherein the vehicle maneuver includes an application of a braking device, a normal descent to a minimum safe altitude, an entry into a holding pattern, a transponder transmission of an emergency code, and an emergency descent profile.

In a further aspect, embodiments of the inventive concepts disclosed herein are directed to a method wherein the variable delay is based on an attitude of the vehicle, a nose position of the vehicle, a speed of the vehicle, an altitude of the vehicle, a time to ground impact of the vehicle, a proximity of the vehicle to a second vehicle, and an anticipated required maneuver of the vehicle.

In a further aspect, embodiments of the inventive concepts disclosed herein are directed to a system for monitoring a capacity of an operator. The system may comprise a processor, a memory operatively connected with the processor, the memory storing non-transitory computer readable program code for monitoring the capacity of the operator, the computer readable program code comprising instructions which, when executed by the processor, cause the processor to perform and direct a plurality of steps including accessing an acceptable range for an operator physical parameter and establishing a data connection with an operator physical monitor configured for measuring the operator physical parameter of an operator of a vehicle.

The system may periodically receive an operator physical parameter via the data connection with the operator physical monitor and compare the received operator physical parameter with the acceptable range. Should the comparison reveal an operator physical parameter outside of the acceptable range, the system may send a first warning to the operator via a warning device. Should the first warning fail to rectify the situation, the system may execute an emergency action if a result of the comparing continues to include an operator physical parameter outside of the acceptable range, the execution of the emergency action after a variable delay. The emergency action may include 1) sending a second warning to the operator, 2) executing a vehicle maneuver to ensure a safety of the vehicle and a safety of the operator, and 3) sending a notification offboard the vehicle, and discontinuing the emergency action based on a receipt of an operator intervention during the variable delay.

In a further aspect, embodiments of the inventive concepts disclosed herein are directed to a system wherein the processor is housed within any of a battery powered portable electronic device, a battery powered electronic flight bag, and an aircraft powered and certified electronic flight bag.

In a further aspect, embodiments of the inventive concepts disclosed herein are directed to a system wherein the processor is further configured for accessing an acceptable range for an operator workspace ambient parameter, establishing a data connection with a workspace ambient monitor configured for measuring the operator workspace ambient parameter, the data connection may be a wired connection and a wireless connection, periodically receiving an operator workspace ambient parameter from the workspace ambient monitor, comparing the operator workspace ambient parameter with the acceptable range, executing the emergency action if a result of the comparing includes an operator workspace ambient parameter outside of the acceptable range, the execution of the emergency action after the variable delay, wherein the workspace ambient monitor is housed within the portable electronic device and configured to receive power from the portable electronic device.

In a further aspect, embodiments of the inventive concepts disclosed herein are directed to a system wherein the operator physical monitor further includes a monitor worn on a wrist of the operator, a monitor worn on a leg of the operator, a monitor worn on an extremity of the operator, a monitor proximal to a skin of the operator, and a monitor attached to a torso of the operator.

In a further aspect, embodiments of the inventive concepts disclosed herein are directed to a system wherein the workspace ambient monitor further includes a portable battery powered monitor configured to be carried by the operator and a sensor installed in the workspace and receiving power from a vehicle power supply.

In a further aspect, embodiments of the inventive concepts disclosed herein are directed to a system wherein the processor is further configured for establishing a data connection with an interactive workspace display, receiving and storing a interactivity rate of the operator with the workspace interactive display, receiving a current interactivity rate from the interactive workspace display, comparing the current interactivity rate with the stored interactivity rate, and including the interactivity rate comparison in the determination of the capacity of the operator.

In a further aspect, embodiments of the inventive concepts disclosed herein are directed to a system the data connection further includes a wired data connection and a wireless data connection with the operator physical monitor.

In a further aspect, embodiments of the inventive concepts disclosed herein are directed to a system wherein the second warning includes an escalation of the first warning, an audio, a visual, a tactile, a physical, and a combination warning directed at the operator, and an increasing urgency of alerts within an embedded display system.

It is to be understood that both the foregoing general description and the following detailed description are exemplary and explanatory only and are not necessarily restrictive of the inventive concepts disclosed herein as claimed. The accompanying drawings, which are incorporated in and constitute a part of the specification, illustrate embodiments of the inventive concepts disclosed herein and together with the general description, serve to explain the principles of the inventive concepts.

BRIEF DESCRIPTION OF THE DRAWINGS

The numerous advantages of the inventive concepts disclosed herein may be better understood by those skilled in the art by reference to the accompanying figures in which.

DETAILED DESCRIPTION

Figure 1:
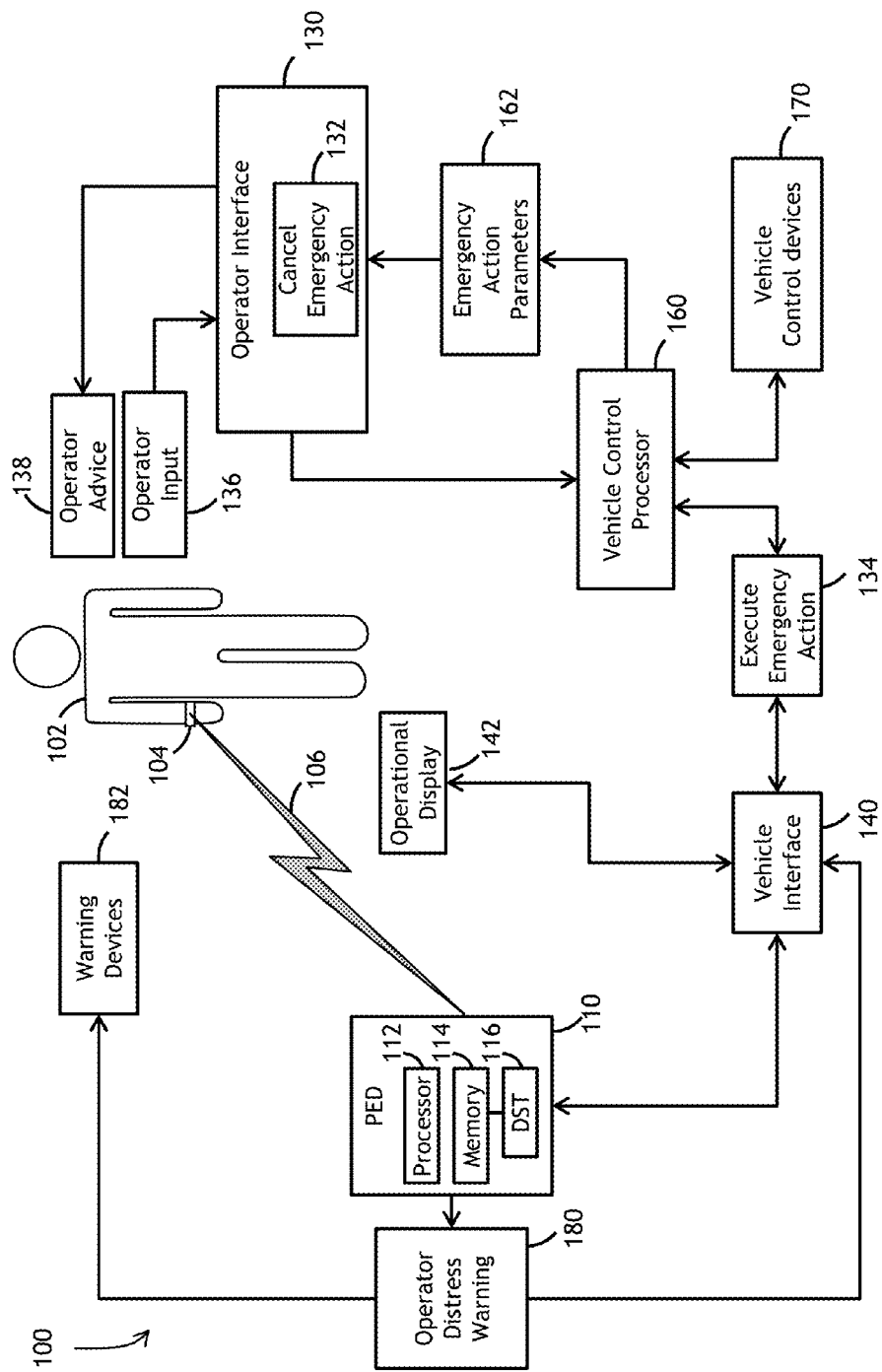
FIG. 1 is a diagram of a system for capacity monitoring of an operator in accordance with an embodiment of the inventive concepts disclosed herein.

Reference will now be made in detail to the presently preferred embodiments of the inventive concepts disclosed herein, examples of which are illustrated in the accompanying drawings.

The following description presents certain exemplary embodiments of the inventive concepts disclosed herein. However, the inventive concepts disclosed herein may be embodied in a multitude of different ways as defined and covered by the claims. In this description, reference is made to the drawings wherein like parts are designated with like numerals throughout.

Embodiments of the inventive concepts disclosed herein are directed to a system and related method for monitoring an operator of a vehicle for signs of incapacity. The system may employ low-cost, consumer electronics to monitor operator vital signs allowing the system to determine when the operator is active and normally operating the vehicle, operating the vehicle under a high workload, and/or has become inactive (potentially incapacitated). The system may also employ low-cost, industrial electronics to monitor ambient workspace temperature, pressure, and oxygen levels and may offer the system a second redundant source of information to detect ambient factors affecting the capacity of the operator. Should operator capacity be in question, the system may warn the operator and take an appropriate safety based action including application of a vehicle control system and eventually assuming control of the vehicle.

| Reference Chart | |
| --- | --- |
| Ref. No. | Description |
| 100 | System for Vehicle Operator |
| 102 | Operator |
| 104 | Operator Physical Monitor |
| 106 | Wireless Monitor Connection |
| 110 | Portable Electronic Device |
| 112 | Processor |
| 114 | Memory |
| 116 | Decision Support Tools |
| 120 | Workspace Ambient Sensor |
| 122 | Wireless Ambient Sensor Connection |
| 130 | Operator Interface |
| 132 | Cancel Emergency Action |
| 134 | Execute Emergency Action |
| 136 | Operator Input |
| 138 | Operator Advice |
| 140 | Vehicle Interface |
| 142 | Operational Display |
| 160 | Vehicle Control Processor |
| 162 | Emergency Action Parameters |
| 170 | Vehicle Control Devices |
| 180 | Operator Distress Warning |
| 182 | Warning Devices |
| 200 | Aircraft Embodiment |
| 202 | Pilot |
| 230 | Up Front Control |
| 236 | Pilot Input |
| 238 | Pilot Advice |
| 240 | Avionics Interface |
| 242 | Horizontal/Vertical Situation Display |
| 244 | Engine-Indicating and Crew-Alerting System (EICAS) |
| 246 | External Ambient Sensor |
| 260 | Autopilot |
| 272 | Flight Controls |
| 274 | Auto throttles |
| 276 | Speed brakes |
| 278 | Wheel Brakes |
| 280 | Pilot Distress Warning |
| 282 | Audio Warning Device |
| 284 | Video Warning Device |
| 286 | Physical Warning Device |
| 300 | Certified Embodiment |
| 310 | Class Three Electronic Flight Bag (EFB) |
| 320 | Certified Sensors |
| 322 | Certified Sensor Connection |
| 360 | Datalink |
| 400 | Flowchart |
| 402 | Receive Parameter Acceptable Range |
| 404 | Connect with 1) Operator monitor 2) ambient sensor |
| 406 | Receive Specific Operator Details |
| 408 | Adjust Parameter Acceptable Range |
| 410 | Monitor Operator and Ambient Parameters |
| 412 | Parameters Adjusted Range |
| 414 | Send Pilot Distress Warning |
| 416 | Workstation Parameters Within Adjusted Range |
| 418 | Begin Countdown |
| 420 | Notify Operator |
| 422 | Operator Intervention |
| 424 | Execute Emergency Action |

As described herein, one exemplary embodiment may include a description of an operator as a pilot and the vehicle as an aircraft. This aircraft embodiment may be one embodiment chosen for exemplary purposes and operates to describe the specifics of the inventive concepts herein. It is contemplated a wide variety of vehicles and operators (e.g., automobiles, trucks, bus, trains, single piloted and multi-piloted vehicles, helicopters and any situation where an incapacity of a single human may cause adverse consequences) may find direct benefit from the inventive concepts disclosed herein.

Referring to FIG. 1, a diagram of a system 100 for capacity monitoring of an operator in accordance with an embodiment of the inventive concepts disclosed herein is shown. The system 100 may include a portable electronic device (PED) 110 configured with a processor 112, a memory 114, and decision support tools associated with the memory 114. An operator 102 may be fitted with an operator physical monitor 104 configured for measuring a physical parameter of the operator 102 and transmitting data indicative of the measured physical parameter to the PED 110 via a wireless monitor connection 106.

In proximity with the operator 102, warning devices 182 may operate to provide a warning to the operator 102, an operator input 136 may receive an input from the operator 102 while an operator advice 138 may be configured to transmit information to the operator 102. An operator interface 130 may function to receive the input from the operator 102 and transmit to a vehicle control processor 160. Also, the operator interface 130 may function to receive emergency action parameters 162 and communicate the emergency action parameters 162 to the operator 102. In addition, the operator interface 130 may function as a medium for which the operator 102 may intervene to cancel the emergency action 132 via an operator input 136.

An operational display 142 may be a display screen configured for providing the operator 102 information relating to the status of the vehicle. A vehicle interface 140 may provide the operational display 142 with vehicle related information as well as receive an additional input from the operator 102.

The PED 110 may provide the housing and power source for the processor 112 to determine whether and when to issue an operator distress warning 180. The operator distress warning 180 may be transmitted to the vehicle interface 140 for transmission to the operational display 142 and to the warning devices 182 to provide the warning to the operator 102.

Prior to an operational state, the PED 110 may receive and store within the memory 114 an acceptable range for the operator physical parameters. The acceptable range may include a maximum and minimum value for each of the operator physical parameters historically applicable to a normal operator in operation of the vehicle. For example, a normal pulse rate, normal perspiration rate for specific phases of operation (e.g., normal workload, high workload) may be specific operator physical parameters monitored by the system 100.

In one embodiment, a pilot may wear the operator physical monitor 104 on the wrist of the hand most often involved in operating the aircraft and avionics systems. For example, a pilot sitting in the left seat may commonly use the right hand to manipulate the throttles, cursor control devices, switches, and knobs in the aisle stand, glare shield control panel, and overhead panel. Conversely, a pilot sitting in the right seat may commonly use the left hand to access these same avionics and aircraft controls and interfaces.

In additional embodiments, the operator physical monitor 104 may be worn on a leg of the operator 102, or worn on an extremity of the operator 102 (e.g., around a finger similar to a ring), a monitor proximal to a skin of the operator 102 (e.g., as an adhesive patch), and a monitor attached to a torso of the operator 102 (e.g., elastically attached around the chest).

In operation, the PED 110 may periodically receive and store to the memory 114 updated measured physical parameters of the operator 102 from the operator physical monitor 104 and compare the currently received measured physical parameters of the operator 102 to those stored in the memory 114. The periodic reception may be commanded by the PED 110 via a signal sent from the PED 110 to the operator physical monitor 104 commanding a response by the operator physical monitor 104 to transmit the measured physical parameters to the PED 110.

In embodiments, the physical parameters of the operator 102 may include a pulse rate, a respiration rate, a skin temperature, an activity level, and a perspiration level. For example, given an acceptable pulse rate range of 60 beats per minute to 120 beats per minute, the processor 112 may compare the received physical parameters of the operator 102 to this acceptable range. Should the current received pulse rate be outside of this range, the processor 112 may determine an operator distress warning 180 and sent the operator distress warning 180 to the warning devices 182 and the vehicle interface 140.

In an additional example, the PED 110 may be a Class 1 or Class 2 Electronic Flight Bag (EFB) configured to host a specific application within the memory 114 able to capture the vital signs measured by the operator physical monitor 104 worn by the operator 102. Preferably, a wrist-worn operator physical monitor 104 may function to measure the physical parameters and activity (motion) level of the operator 102, but additional types of activity monitors are contemplated within the scope of the inventive concepts disclosed herein.

The Decision Support Tools (DST) 116 stored within the memory 114 and accessible by the processor 112 may include additional sources of determination of the presence of an operator distress and incapacity. Additionally, the DST 116 may include additional economic motivation for the operator 102 to bring the PED 110 onboard the vehicle. For example, a safety management team or an insurance carrier may operate to encourage each operator 102 to only operate the vehicle with the PED 110 in operation and continuously monitoring the capacity of the operator 102. Integration of the system 100 operator capacity monitoring with these additional DST 116 may enable these tools to tailor their operations in appropriate ways based upon specific operator stress.

For example, a single operator 102 of a tour bus may experience an increased pulse rate coupled with an increased movement of one or both of the hands during driving through the mountains. The increased workload may indicate to the system 100 the single operator 102 may be experiencing stress and require an operator distress warning 180. Here, the tour bus driver DST 116 may differ from those DST 116 used to monitor the single operator 102 of the locomotive (e.g., hand motion, accelerometer readings).

In operation, the system 100 may measure heart rate, body temperature, perspiration levels, and motion (using accelerometers), and compare the stored parameters with the measured parameters to determine:

1) Periods of high workload: for example, an increased heart rate, increased body temperature, increased perspiration, and increased motion of the commonly used hand;

2) Periods of inactivity (possibly indicating operator inattentiveness and/or sleepiness): for example, a decreased heart rate, decreased body temperature, decreased perspiration, and decreased motion of the commonly used hand; and 3) Oxygen deprivation: for example, an increased heart-rate coupled with decreased motion (and possibly slow, uncoordinated, or chaotic motion) of the commonly used hand.

The operator physical monitor 104 may allow the system 100 detection of at least three conditions which may affect the continued safe operation of the vehicle: 1) stress caused by high workloads; 2) loss of attention caused by low workloads; and 3) oxygen deprivation caused by a slow depressurization event that has gone undetected by other means.

In embodiments, the system 100 may operate to provide the operator distress warning 180 for at least three exemplary conditions:

Response 1)

During periods of high work load, the PED 110 may provide suggestions for further operator action; this may reduce workload and may help to break the operator 102 out of the a possible tunnel vision scenario that may occur during high stress situations. The operator physical monitor 104 may measure and transmit an increase pulse rate and increased perspiration rate. One possible suggestion for further action may be to "slow down" displayed on the operational display 142 for this high workload scenario.

Response 2)

If the operator 102 has become inattentive (or even fallen asleep), (e.g., the operator physical monitor 104 is measuring a reduced pulse rate coupled with a reduced respiration rate) the system 100 may issue an escalating series of operator distress warnings 180 (first a textual warning on the operational display 140 (e.g., Warning—confirm you are awake?); then text and audio tones via the warning devices 182; then text and speech via the warning devices 182) to get the attention of the operator 102 and to request an acknowledgement Response 3)

The system 100 may begin with an escalating series of alerts (e.g., notification, cautions, and warnings) via the operational display 142 and the warning devices 182 followed by a delayed automated execution of an emergency action 134 via an application of the vehicle control devices 170. The emergency action 134 may include such actions as a reduction of a power source of the vehicle to idle, an application of a braking device associated with a wheeled vehicle, and application of an emergency descent to a safe altitude where the vehicle may be an aircraft.

For example, emergency action parameters 162 may include an application of a braking device such as a wheel brake on a semi-truck, a normal descent to a minimum safe altitude in the case of an incapacitated operator 102, an entry into a holding pattern, a transmission of an emergency signal, and an emergency descent profile in the case of a rapid depressurization event.

Should the operator 102 desire the system 100 to refrain from automated execution of the emergency action 134, the operator 102 may cancel the emergency action 132 at any time with the cancel emergency action 132 via operator interface 130.

Figure 2:
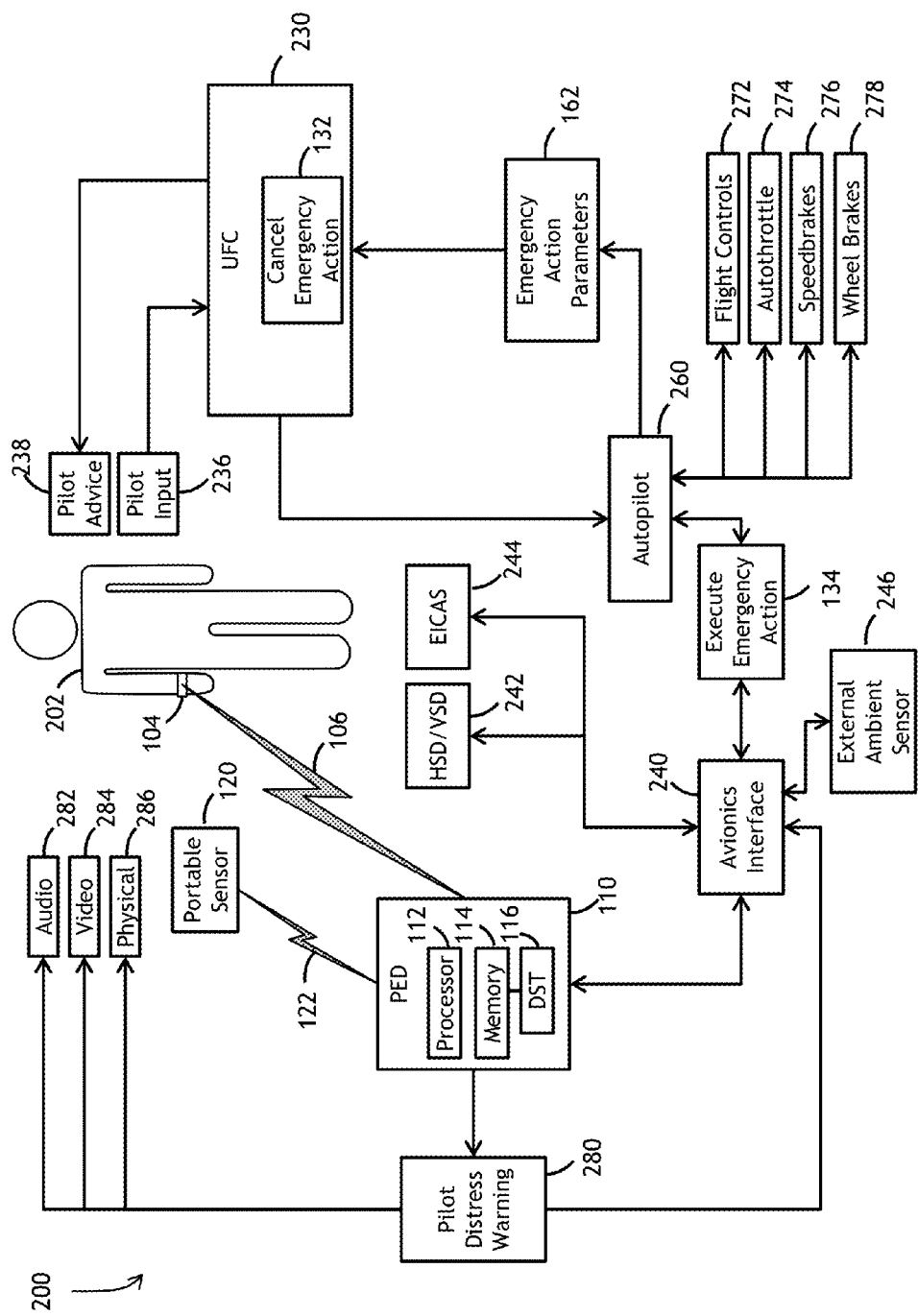
FIG. 2 is a diagram of a system for capacity monitoring of a pilot operator in accordance with an embodiment of the inventive concepts disclosed herein.

Referring to FIG. 2, a diagram of a system 200 for capacity monitoring of a pilot operator in accordance with an embodiment of the inventive concepts disclosed herein is shown. An aircraft embodiment system 200 sited onboard an aircraft may operate with similar function as the system 100.

The system 200 may include the PED 110 configured to receive the wireless signal 106 from the operator physical monitor 104 in addition, the PED 110 may be further configured to receive a wireless signal 122 transmitted from a workspace ambient sensor 120. The workspace ambient sensor 120 may be configured for sensing an ambient parameter within the workspace occupied by the pilot 202. For example, the workspace ambient sensor 120 may operate to sense, inter alia, an air temperature, a pilot motion level, an air pressure, a humidity level, acceleration, and an oxygen level within the workspace (cockpit and within the pressure hull of the aircraft).

The workspace ambient sensor 120 may operate as a stand-alone device configured for portability with its own battery power source. Alternatively, the workspace ambient sensor 120 may be configured within the PED 110 and share a common power source with the PED 110. Also, the workspace ambient sensor 120 may be connectable to the PED 110 via a combination power and data cable connection. For example, a Universal Serial Bus (USB) data connection may enable the PED 110 to provide power to as well as receive data from the workspace ambient sensor 120.

Additionally, Embedded Display System (EDS) elements Horizontal/Vertical Situation Display 242 and Engine-Indicating and Crew-Alerting System (EICAS) 244 may operate not only as a traditional interface between the pilot 202 and the avionics interface 240, but also as an additional source of the pilot distress warning 280 presented to the pilot 202.

Further, the EDS elements may function as an additional source for early recognition of pilot incapacity. Should a phase of flight require frequent interaction between the pilot 202 and the HSD 242, and the PED 110 may detect zero interaction by the pilot 202, this indication may be an additional DST 116 for the PED 110 to issue the pilot distress warning 280.

An external ambient sensor 246 may operate to provide an additional DST 116 to the PED 110 to issue a pilot distress warning 280. The external ambient sensor 246 may operate to sense the environment external to the workspace (e.g., outside the pressure hull of an aircraft, outside the cab of a truck). Should a combination of sensors including the operator physical sensor 104 and the external ambient sensor 246 indicate a measurement outside the acceptable range, the PED 110 may operate to issue the pilot distress warning 280.

Flight controls 272 including ailerons, rudder and elevator may be positioned by the autopilot 260 as the autopilot may be actively controlling the aircraft. Also, the autothrottles 274 may function to provide a power setting to the engines, speedbrakes 276 may provide the autopilot with additional drag while wheel brakes 278 may provide stopping power while the aircraft is on a runway.

In embodiments, the system 200 may receive an input associated with a pilot specific detail from the operator physical monitor 104. Based on the operator specific detail, the system 200 may adjust the acceptable range of operator physical parameters for the specific pilot 202. For example, a pilot 202 who is an avid runner may maintain a resting pulse rate lower than a pilot 202 who may have an increased body mass index and is a smoker. In this manner, the system 200 may tailor the operation of the pilot distress warning 280 to the specific pilot 202. Further, the adjustment to the acceptable range may be an adjustment of zero for an average operator or pilot 202.

In addition, the aircraft embodiment system 200 may adjust the acceptable range of the operator physical parameters based on an operational phase of vehicle (e.g., a phase of flight). For example, an increase in heart rate and an increase in blood pressure may be anticipated in a high workload environment (e.g., weapons delivery, air combat, or severe turbulence). The aircraft embodiment system 200 may adjust the acceptable range based on this anticipated increase in the operator physical parameters.

Additional warning devices including an audio warning device 282, a video warning device 284, and a physical warning device 286, one or more of which may operate to provide the pilot 202 with the pilot distress warning 280 issued by the PED 110. For example, one physical warning device 286 may include a vibration device and/or a periodic motion device associated with the seat of the pilot 202. In addition, the operator physical monitor 104 may function to rouse a sleeping or semi-conscious pilot 202 via the physical warning device 286 via a vibratory or pulsed response. In further embodiments, the operator physical monitor 104 may operate as a warning device via a vibration, pulse, and/or electric shock within the operator warning device 104.

An upfront control 230 may operate as an interface between a pilot input 236 and a pilot advice 238 and the autopilot 260. Integration of the pilot input 236 into the upfront controls 230 may offer an immediate access to the system 200 for the pilot 202. Some upfront controls 230 may include a master warning and master caution as well as easy access to commonly used features such as autopilot 260 controls, communication tools, and approach mode settings.

The aircraft embodiment of system 200 may operate to provide increasing warnings to the pilot 202 via the warning systems 282-286 while attempting to bring the incapacitated pilot 202 back into the flying role. The system 200 may begin a variable delay before executing the emergency action 134. The delay may be directly proportional to the situation in which the aircraft is currently flying.

For example, if the aircraft is in straight and level flight at 42,000 feet Mean Seal Level (MSL), and the operator physical monitor 104 reveals a reduced pulse rate, the workspace ambient sensor 120 reveals a reduction in oxygen level in the cockpit, the external ambient sensor 246 reveals an actual altitude of 42,000 feet MSL, and the workspace ambient sensor 120 also reveals a reduction in temperature, the PED 110 may use the DST 116 to determine a loss of cabin pressure is occurring. In this situation, the PED 110 may issue the pilot distress warning 280 and, followed by a 15 second variable delay for operator intervention, execute an emergency descent to 10,000 feet MSL as the appropriate emergency action 132. Here the PED 110 may direct the autopilot 260 to reduce the autothrottles 274 to idle, extend the speedbrakes 276 to a maximum deflection, and adjust the flight controls 272 for a nose down profile of an emergency descent.

Conversely, should the aircraft be operating in a combat environment in a 45 degree dive delivering weapons with only seconds to ground impact, the variable delay may be reduced to an exemplary two seconds of inactivity and reduced physical parameters before the system 200 may execute the emergency action. Also here, the emergency action may be considerably different and may include a command to the autopilot 260 to roll to wings level, an increase in the autothrottles 274 to climb power, and a commanded nose up attitude to climb to 10,000 feet MSL and level flight. Once in level flight, the system 200 may continue to send warnings to the pilot 202 and send a distress signal offboard the aircraft to a command authority for assistance.

Embodiments of the system 200 may also be tailored to a desired Design Assurance Level (DAL). A low DAL system 200 may request the autopilot perform the appropriate emergency action. However, a high DAL automated system may operate to confirm the pilot 202 is incapacitated prior to starting the descent (e.g., issuing the pilot distress warning 280 and implementing a delay timer to give the pilot 202 an option to cancel the emergency action).

Figure 3:
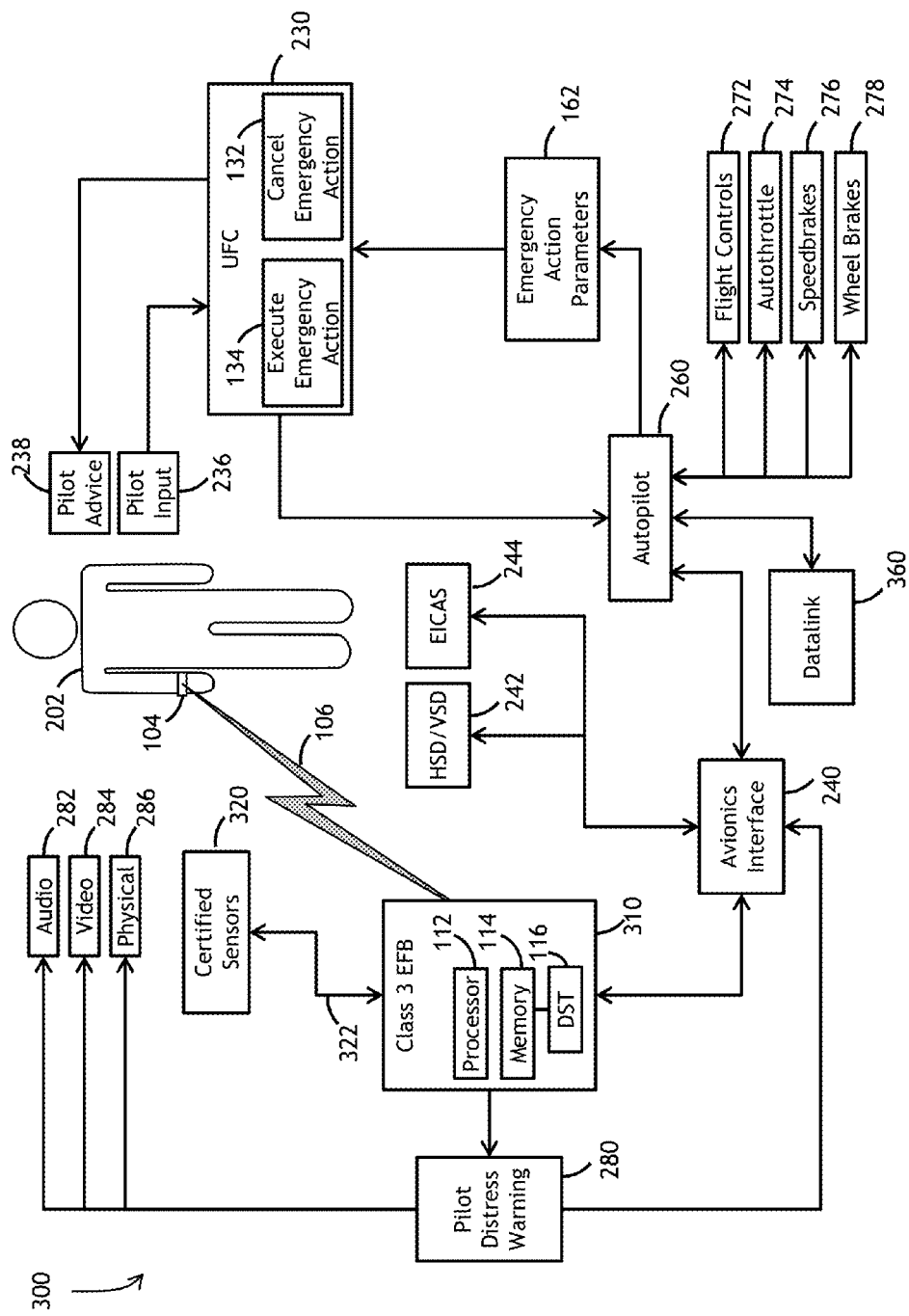
FIG. 3 is a diagram of a system for capacity monitoring of a pilot exemplary of an embodiment of the inventive concepts disclosed herein.

Referring to FIG. 3, a diagram of a certified system 300 for capacity monitoring of a pilot exemplary of an embodiment of the inventive concepts disclosed herein is shown. The certified system 300 may include a certified sensor 320 as the workspace ambient sensor suite. Certification of installed system onboard an aircraft may include additional steps to ensure operational applicability and compliance with rigorous performance standards. Certified sensors 320 may be coupled with a class three EFB 310 (also certified) via a certified sensor connection 322.

Also, the certified sensors 320 may be sited within the workspace in a variety of locations around the pilot 202. For example, a motion detector may be sited directly above the pilot 202 and configured for sensing the motion of the pilot 202 from above while one or more temperature and pressure sensors may be placed throughout the cockpit to aid in redundant operation of the certified system 300.

Within the certified system 300, additional high DAL system level functional safeguards may be in place within the certified avionics and autopilot 260 to ensure any disagreement between the class three EFB and the certified avionics results in a conservative action. For example, a high integrity certified avionics may perform a final analysis to determine if an emergency event is present and emergency action is warranted.

In an additional embodiment, the certified system 300 may operate in coordination with a datalink 360 to send and receive data offboard the aircraft. The datalink 360 may be directly associated with the autopilot 260 and configured to receive flight control inputs from a source offboard the aircraft. In this manner, should the pilot 202 become permanently incapacitated, an offboard control entity may operate the control surfaces of the aircraft and execute further emergency actions to ensure safety of the aircraft, passengers and cargo.

Figure 4:
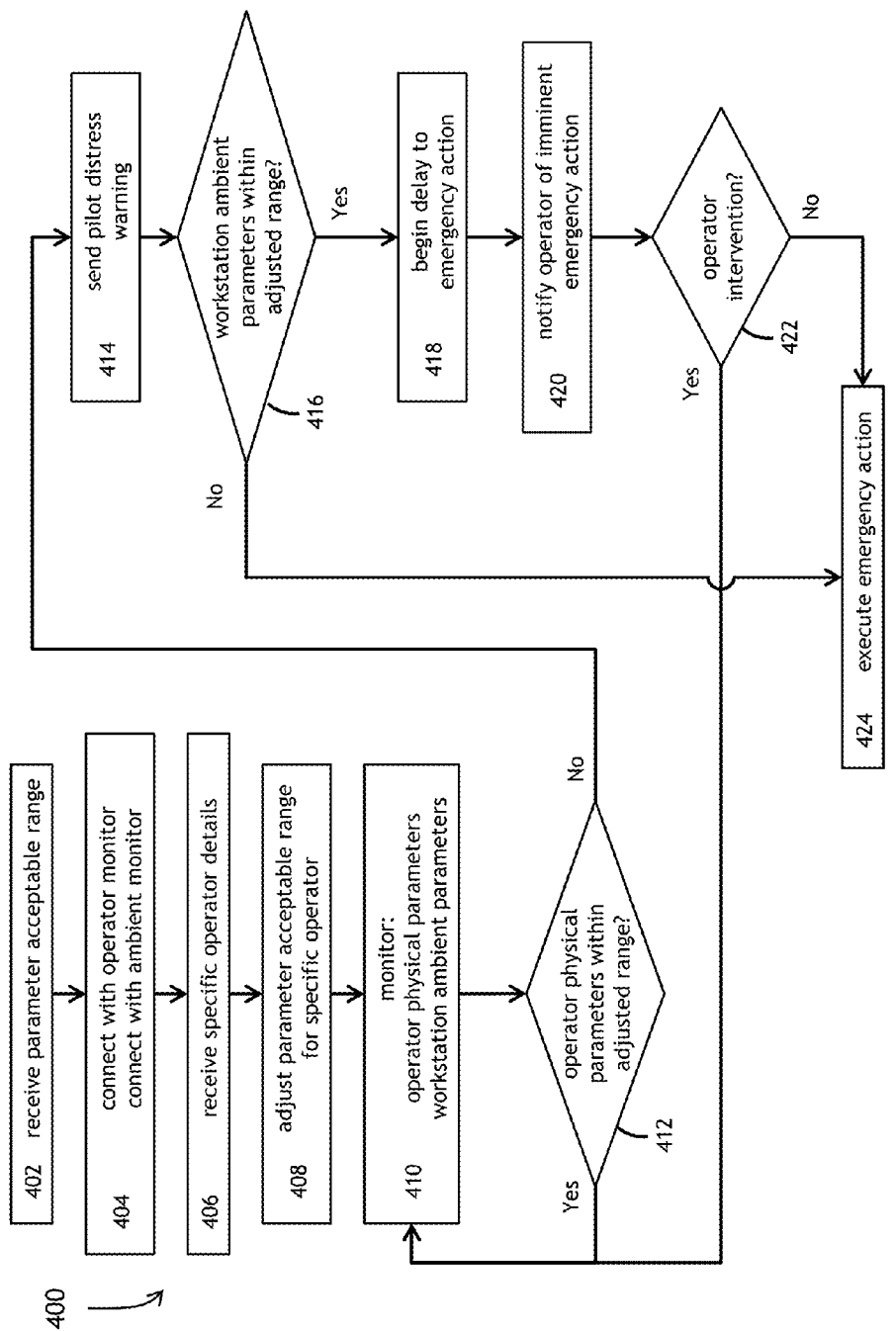
FIG. 4 is a flow diagram of a method for operator capacity monitoring exemplary of one embodiment of the inventive concepts disclosed herein.

Referring to FIG. 4, a flow diagram of a method 400 for operator capacity monitoring exemplary of one embodiment of the inventive concepts disclosed herein is shown. The method 400 for monitoring the capacity of an operator may include, at a step 402, receiving a parameter acceptable range, and at a step 404, connecting with an operator physical monitor as well as with a workspace ambient monitor. The method 400 may, at a step 406, receive specific operator details and, at a step 408, adjust the parameter acceptable range based on the received details associated with the operator.

The method may continue at a step 410 with monitoring each of the operator physical parameters and the workstation ambient parameters. At a step 412, the method may compare the received operator physical parameters with the stored and adjusted acceptable range and, if within the range, the method may continue to monitor at the step 410. However, if the operator physical parameters are outside the acceptable range, the method may, at a step 414, send a pilot distress warning to the operator. The method may, at a step 416, compare the workstation ambient parameters to the acceptable range. Should the result of the query 416 be negative, the method may flow (after a delay) directly to a step 424 of execution of an emergency action.

However, if the workspace parameters are within the acceptable range at the step 416, the method may, at a step 418, begin a delay countdown to the execution of the emergency action and, at a step 420, notify the operator of an imminent emergency action. The method may check for operator intervention at a step 422 and, receiving no operator intervention, the method may, at the step 424, execute the emergency action. Should the method receive an operator intervention, the method may return to the monitoring step 410.

CONCLUSION

Specific blocks, sections, devices, functions, processes, and modules may have been set forth. However, a skilled technologist will realize that there are many ways to partition the system, and that there are many parts, components, processes, modules or functions that may be substituted for those listed above.

Those having skill in the art will recognize that the state of the art has progressed to the point where there may be little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs.

Additionally, implementations of embodiments disclosed herein may include executing a special-purpose instruction sequence or invoking circuitry for enabling, triggering, coordinating, requesting, or otherwise causing one or more occurrences of virtually any functional operations described herein.

While particular aspects of the inventive concepts disclosed herein have been shown and described, it will be apparent to those skilled in the art that, based upon the teachings herein, changes and modifications may be made without departing from the inventive concepts described herein and their broader aspects and, therefore, the appended claims are to encompass within their scope all such changes and modifications as are within the broad scope of the inventive concepts described herein.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently.

What is claimed is:

1. A method for monitoring a capacity of an operator, comprising:
   receiving an acceptable range for at least one external ambient parameter;
   establishing a data connection with at least one ambient monitor configured for measuring the at least one external ambient parameter;
   receiving the external ambient parameter from the at least one ambient monitor;

comparing the external ambient parameter to the acceptable range;
sending the first warning to the operator via the at least one warning device if a result of the comparing includes an external ambient parameter outside the acceptable range;
accessing an acceptable range for at least one operator physical parameter;
establishing a data connection with at least one operator physical monitor configured for measuring the at least one operator physical parameter of an operator of a vehicle;
periodically receiving at least one operator physical parameter via the data connection with the at least one operator physical monitor;
comparing the received at least one operator physical parameter with the acceptable range;
sending a first warning to the operator via at least one warning device if a result of the comparing includes at least one operator physical parameter outside of the acceptable range;
executing an emergency action if a result of the comparing includes at least one operator physical parameter outside of the acceptable range, the execution of the emergency action after a variable delay, the emergency action including at least one of: 1) sending a second warning to the operator, 2) executing a vehicle maneuver to ensure a safety of the vehicle and a safety of the operator, and 3) sending a notification offboard the vehicle; and
discontinuing the emergency action based on a receipt of an operator intervention during the variable delay.

2. The method of claim 1, further including:
acquiring at least one operator specific detail, the at least one operator specific detail acquired via at least one of: the data connection with at least one operator physical monitor, an input from the operator, and a memory;
acquiring an operational status of the vehicle; and
adjusting the acceptable range based on one of: the at least one received operator specific detail and the operational status of the vehicle.

3. The method of claim 1, further including:
accessing an acceptable range for at least one operator workspace ambient parameter;
establishing a data connection with at least one workspace ambient monitor configured for measuring the at least one operator workspace ambient parameter;
periodically receiving at least one operator workspace ambient parameter from the at least one workspace ambient monitor;
comparing the at least one operator workspace ambient parameter with the acceptable range; and
executing the emergency action if a result of the comparing includes 1) at least one operator workspace ambient parameter outside of the acceptable range and 2) at least one operator physical parameter outside of the acceptable range, the execution of the emergency action after the variable delay.

4. The method of claim 1, wherein the at least one operator physical parameter further includes at least one of: a pulse rate, a respiration rate, a skin temperature, an activity level, and a perspiration level.

5. The method of claim 3, wherein the at least one operator workspace ambient parameter further includes at least one of an air temperature, a motion level, an air pressure, a humidity level, and an oxygen level.

6. The method of claim 1, further including:
establishing a data connection with at least one interactive workspace display onboard the vehicle;
accessing an acceptable interactivity rate for the operator with the at least one interactive workspace display, the acceptable interactivity rate including a phase of operations of the vehicle;
receiving a current interactivity rate from the at least one interactive workspace display;
comparing the current interactivity rate with the acceptable interactivity rate; and
sending the first warning to the operator via the at least one warning device if a result of the comparing includes a current interactivity rate outside the acceptable interactivity rate for the phase of operations.

7. The method of claim 1, wherein the vehicle maneuver includes one of: an application of a braking device, a normal descent to a minimum safe altitude, an entry into a holding pattern, a transponder transmission of an emergency code, and an emergency descent profile.

8. The method of claim 1, wherein the variable delay is based at least on one of: an attitude of the vehicle, a nose position of the vehicle, a speed of the vehicle, an altitude of the vehicle, a time to ground impact of the vehicle, a proximity of the vehicle to a second vehicle, and an anticipated required maneuver of the vehicle.

9. A system for monitoring a capacity of an operator, comprising:
at least one processor;
a memory operatively connected with the at least one processor;
the memory storing non-transitory computer readable program code for monitoring the capacity of the operator, the computer readable program code comprising instructions which, when executed by the at least one processor, cause the at least one processor to perform and direct the steps of:
receiving an acceptable range for at least one external ambient parameter;
establishing a data connection with at least one ambient monitor configured for measuring the at least one external ambient parameter;
receiving the external ambient parameter from the at least one ambient monitor;
comparing the external ambient parameter to the acceptable range;
sending the first warning to the operator via the at least one warning device if a result of the comparing includes an external ambient parameter outside the acceptable range;
accessing an acceptable range for at least one operator physical parameter;
establishing a data connection with at least one operator physical monitor configured for measuring the at least one operator physical parameter of an operator of a vehicle;
periodically receiving at least one operator physical parameter via the data connection with the at least one operator physical monitor;
comparing the received at least one operator physical parameter with the acceptable range;
sending a first warning to the operator via at least one warning device if a result of the comparing includes at least one operator physical parameter outside of the acceptable range;
executing an emergency action if a result of the comparing includes at least one operator physical parameter outside of the acceptable range, the execution of the emergency action after a variable delay, the emergency action including at least one of: 1) sending a second warning to the operator, 2) executing a vehicle maneuver to ensure a safety of the vehicle and a safety of the operator, and 3) sending a notification offboard the vehicle; and discontinuing the emergency action based on a receipt of an operator intervention during the variable delay.

10. The system of claim 9, wherein the at least one processor is housed within at least one of: a battery powered portable electronic device, a battery powered electronic flight bag, and an aircraft powered and certified electronic flight bag.

11. The system of claim 9, wherein the at least one processor is further configured for:

accessing an acceptable range for at least one operator workspace ambient parameter;

establishing a data connection with at least one workspace ambient monitor configured for measuring the at least one operator workspace ambient parameter, the data connection one of: a wired connection and a wireless connection;

periodically receiving at least one operator workspace ambient parameter from the at least one workspace ambient monitor;

comparing the at least one operator workspace ambient parameter with the acceptable range;

executing the emergency action if a result of the comparing includes at least one operator workspace ambient parameter outside of the acceptable range, the execution of the emergency action after the variable delay;

wherein the at least one workspace ambient monitor is housed within the portable electronic device and configured to receive power from the portable electronic device.

12. The system of claim 9, wherein the at least one operator physical monitor further includes at least one of a monitor worn on a wrist of the operator, a monitor worn on a leg of the operator, a monitor worn on an extremity of the operator, a monitor proximal to a skin of the operator, and a monitor attached to a torso of the operator.

13. The system of claim 11, wherein the at least one workspace ambient monitor further includes one of a portable battery powered monitor configured to be carried by the operator and a sensor installed in the workspace and receiving power from a vehicle power supply, and wherein the at least one operator workspace ambient parameter further includes at least one of an air temperature, a motion level, an air pressure, a humidity level, and an oxygen level.

14. The system of claim 9, wherein the at least one operator physical parameter further includes at least one of: a pulse rate, a respiration rate, a skin temperature, an activity level, and a perspiration level.

15. The system of claim 9, wherein the at least one processor is further configured for:

establishing a data connection with at least one interactive workspace display onboard the vehicle;

accessing an acceptable interactivity rate for the operator with the at least one interactive workspace display, the acceptable interactivity rate including a phase of operations of the vehicle;

receiving a current interactivity rate from the at least one interactive workspace display;

comparing the current interactivity rate with the acceptable interactivity rate; and sending the first warning to the operator via the at least one warning device if a result of the comparing includes a current interactivity rate outside the acceptable interactivity rate for the phase of operations.

16. The system of claim 9, wherein the data connection further includes one of a wired data connection and a wireless data connection with the at least one operator physical monitor.

17. The system of claim 9, wherein the vehicle maneuver includes one of: an application of a braking device, a normal descent to a minimum safe altitude, an entry into a holding pattern, a transponder transmission of an emergency code, and an emergency descent profile.

18. The system of claim 9, wherein the second warning includes at least one of:

an escalation of the first warning;

an audio, a visual, a tactile, a physical, and a combination warning directed at the operator; and an increasing urgency of alerts within an embedded display system.

19. The system of claim 9, wherein the variable delay is based at least on one of: an attitude of the vehicle, a nose position of the vehicle, a speed of the vehicle, an altitude of the vehicle, a time to ground impact of the vehicle, a proximity of the vehicle to a second vehicle, and an anticipated required maneuver of the vehicle.

* * * * *